United States Patent
Yang et al.

(10) Patent No.: US 11,579,175 B2
(45) Date of Patent: Feb. 14, 2023

(54) PULSE MEASUREMENT DEVICE

(71) Applicant: National Cheng Kung University, Tainan (TW)

(72) Inventors: Ching-Lung Yang, Tainan (TW); Chia-Hui Chen, Tainan (TW)

(73) Assignee: National Cheng Kung University, Tainan (TW)

( * ) Notice: Subject to any disclaimer, the term of this patent is extended or adjusted under 35 U.S.C. 154(b) by 33 days.

(21) Appl. No.: 17/212,132

(22) Filed: Mar. 25, 2021

(65) Prior Publication Data
US 2021/0325436 A1   Oct. 21, 2021

(30) Foreign Application Priority Data

Apr. 16, 2020 (TW) ................................ 10911287.5

(51) Int. Cl.
*G01R 23/04* (2006.01)
*G01R 23/07* (2006.01)
*A61B 5/024* (2006.01)

(52) U.S. Cl.
CPC ............. *G01R 23/04* (2013.01); *G01R 23/07* (2013.01); *A61B 5/024* (2013.01)

(58) Field of Classification Search
CPC .......... G01R 23/04; G01R 23/07; A61B 5/024
See application file for complete search history.

(56) References Cited

U.S. PATENT DOCUMENTS

2019/0175117 A1* 6/2019 Tseng .................... H01Q 5/328

* cited by examiner

*Primary Examiner* — Minh Q Phan
(74) *Attorney, Agent, or Firm* — Rabin & Berdo, P.C.

(57) ABSTRACT

A pulse measurement device is provided, including a first signal source, a second signal source, two microwave resonators, two mixers, and a signal processing unit. The first signal source and the second signal source output a first high-frequency signal and a second high-frequency signal, respectively. Each of the microwave resonators generates an electric field according to the first high-frequency signal, and senses a variation in the electric field which is interfered by a pulse to obtain a sensing signal. Each of the mixers is coupled to one of the microwave resonators, to mix the sensing signal and the second high-frequency signal to output a down-converted signal. The signal processing unit respectively demodulates amplitudes of the down-converted signals of the two mixers to obtain amplitude signals.

10 Claims, 3 Drawing Sheets

PULSE MEASUREMENT DEVICE

CROSS-REFERENCE TO RELATED APPLICATION

This non-provisional application claims priority under 35 U.S.C. § 119(a) to Patent Application No. 109112875 filed in Taiwan, R.O.C. on Apr. 16, 2020, the entire contents of which are hereby incorporated by reference.

BACKGROUND

Technical Field

The present invention relates to a measuring device, and in particular, to a device for measuring a pulse through a microwave resonator, and a high-order measurement signal processing method.

Related Art

At present, there are many methods for measuring a pulse state, for example, photoplethysmography (PPG), ultrasound, nuclear magnetic resonance, and the like. However, the methods have problems such as expensive devices and susceptibility to the external environment. The existing measurement technology through microwave is mainly the measurement method of frequency offset, which requires complex detection devices, and because the technology needs enough time to sweep frequency, the detection sensitivity cannot be improved, and the sampling rate of detection signals cannot be improved.

SUMMARY

In view of this, embodiments of the present invention provide a pulse measurement device, including: a first signal source, a second signal source, two microwave resonators, two mixers, and a signal processing unit. The first signal source and the second signal source respectively output a first high-frequency signal and a second high-frequency signal. Each of the microwave resonators is coupled to the first signal source, to form an electric field according to the first high-frequency signal, and senses a variation in the electric field which is interfered by a pulse to obtain a sensing signal. The two mixers are coupled to the second signal source, and each of the mixers is coupled to one of the two microwave resonators, to mix the sensing signal and the second high-frequency signal to output a down-converted signal. The signal processing unit is coupled to the two mixers, to respectively demodulate amplitudes of the down-converted signals of the two mixers to obtain amplitude signals.

In some embodiments, the signal processing unit includes two amplitude demodulators and an analysis device. Each of the amplitude demodulators is coupled to one of the two mixers to demodulate the amplitude of the down-converted signal to obtain an amplitude signal. The analysis device is coupled to the two amplitude demodulators, to obtain, according to the amplitude signals output by the two amplitude demodulators, time points at which the pulse respectively passes through the two microwave resonators.

In some embodiments, the amplitude demodulator is an envelope detector.

In some embodiments, the signal processing unit squares the down-converted signal and performs low-pass filtering to obtain the amplitude signal.

In some embodiments, the down-converted signal is a low intermediate frequency signal.

In some embodiments, the microwave resonator is a split-ring resonator or a complementary split-ring resonator.

In some embodiments, the microwave resonator is an interdigital capacitor shape resonator.

In some embodiments, the interdigital capacitor shape resonator includes two interdigital conductive portions opposite to each other, a gap that continuously bends and extends is jointly defined between the two interdigital conductive portions, and one slot extends from each of two ends of the gap.

In some embodiments, the slots at the two ends of the gap surround two sides of the two interdigital conductive portions.

In some embodiments, the slot is U-shaped.

Based on the above, according to the pulse measurement device provided by the embodiments of the present invention, the signal can be amplified through intermodulation, so that the accuracy of measured data can be improved, the error can be reduced, and the detection sensitivity can be improved through amplitude demodulation. Moreover, the two microwave resonators can be disposed at a local position, which is convenient for a user to place. In addition, the microwave resonator with the interdigital capacitor shape resonator can provide a better induced electric field, increase intensity of the sensing signal, and is more suitable for the user to use.

DETAILED DESCRIPTION

Figure 1:
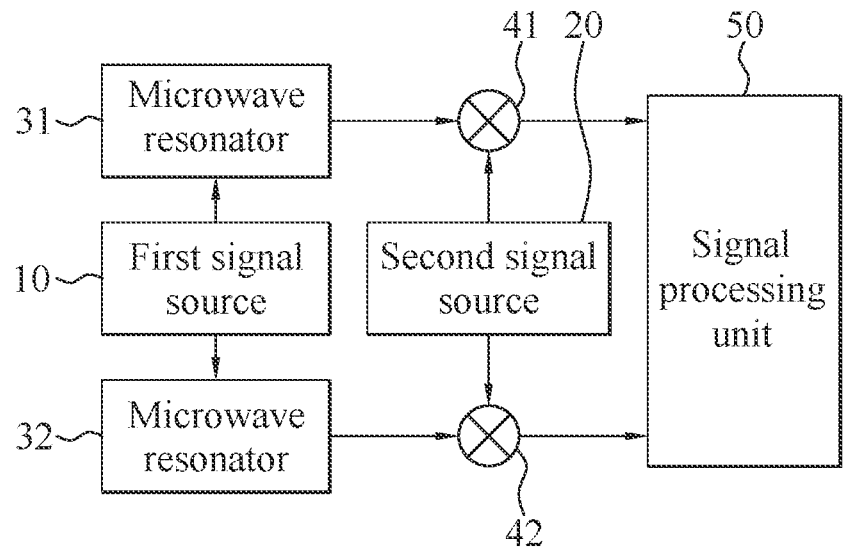
FIG. 1 is a schematic block diagram of a pulse measurement device according to an embodiment of the present invention.

FIG. 1 is a schematic block diagram of a pulse measurement device according to an embodiment of the present invention. The pulse measurement device includes a first signal source 10, a second signal source 20, two microwave resonators 31 and 32, two mixers 41 and 42, and a signal processing unit 50.

The first signal source 10 outputs a first high-frequency signal. The second signal source 20 outputs a second high-frequency signal. A frequency of the first high-frequency signal is quite close to a frequency of the second high-frequency signal, but the two frequencies are different. In an embodiment, the frequency of the first high-frequency signal is 2.45 GHz, and the frequency of the second high-frequency signal is 2.44999 GHz.

The microwave resonators 31 and 32 are devices that store an electric field and magnetic field energy in a limited space. The microwave resonators 31 and 32 are coupled to the first signal source 10 to receive the first high-frequency signal. The microwave resonators 31 and 32 form the electric field according to the first high-frequency signal. When a sensing object (a pulse herein) is in a resonant cavity, an equivalent dielectric constant and permeability in the resonant cavity will suffer perturbance. If there are different designs, sensing may be performed according to the change of a near-field electric field leaking out of the resonant cavity or the same principle. Therefore, characteristics of the sensing object can be learned by analyzing sensing signal obtained by sensing, by the microwave resonators 31 and 32, a variation in the electric field which is interfered by a pulse. Specifically, frequency offset of the sensing signal can be analyzed to detect a pulsation. However, the measurement frequency needs large instruments such as a network analyzer, and the sampling frequency cannot be increased due to the requirement of frequency sweeping. Therefore, in this embodiment of the present invention, the pulsation is detected by analyzing the amplitude change of the sensing signal, in comparison, which has the advantages of easy detection and high measurement sensitivity.

In this embodiment of the present invention, a low intermediate frequency (Low IF) architecture is adopted to perform down-conversion on the sensing signal. The two mixers 41 and 42 are coupled to the second signal source 20, and each of the mixers 41 and 42 is coupled to one of the two microwave resonators 31 and 32 (that is, the mixer 41 is coupled to the microwave resonator 31, and the mixer 42 is coupled to the microwave resonator 32), to mix the sensing signal and the second high-frequency signal to output a down-converted signal. The signal processing unit 50 is coupled to the two mixers 41 and 42, to respectively demodulate amplitudes of the down-converted signals of the two mixers 41 and 42 to obtain amplitude signals.

Figure 2:
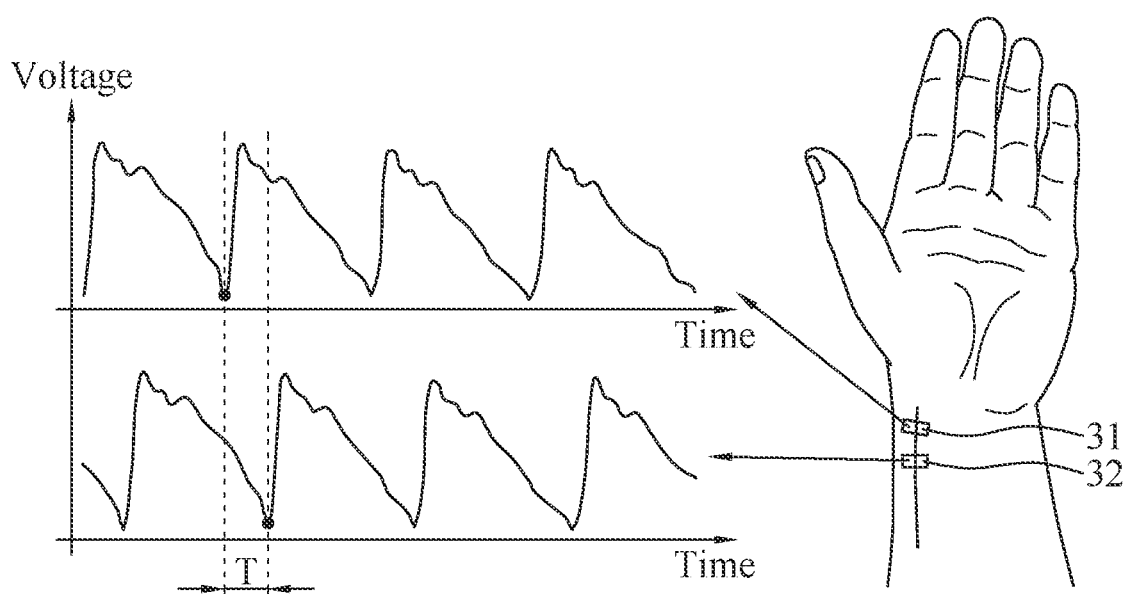
FIG. 2 is a schematic diagram of usage and an amplitude signal of a pulse measurement device according to an embodiment of the present invention.

FIG. 2 is a schematic diagram of usage and an amplitude signal of a pulse measurement device according to an embodiment of the present invention. A pulse herein refers to a pulse of arterial contraction caused by systole. The two microwave resonators 31, 32 are disposed at the radial artery on a wrist. As described in the above embodiment of the present invention, the method has high measurement sensitivity. The two microwave resonators 31 and 32 can be placed quite close to each other, and a time for which the pulse passes between the two microwave resonators is only in millisecond. Therefore, the microwave resonator is quite convenient for a user to wear. A difference between times for which the pulse passes through the two microwave resonators 31 and 32 may be obtained according to a time difference T between valleys of two amplitude signals, but this embodiment of the present invention is not limited thereto. For example, a difference between times for which the pulse passes through the two microwave resonators 31 and 32 may alternatively be obtained according to a time difference between peaks of two amplitude signals.

Figure 3:
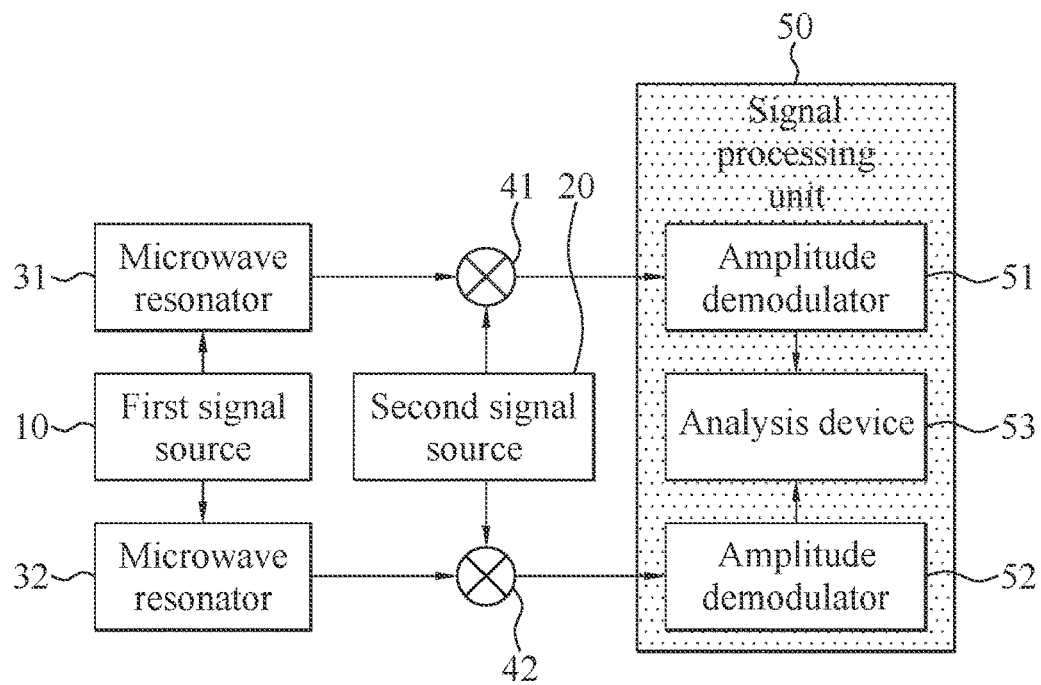
FIG. 3 is a schematic block diagram of a pulse measurement device according to another embodiment of the present invention.

FIG. 3 is a schematic block diagram of a pulse measurement device according to another embodiment of the present invention. In comparison to FIG. 1, a signal processing unit 50 of the present embodiment includes two amplitude demodulators 51 and 52 and an analysis device 53. Each of the amplitude demodulators 51 and 52 is coupled to one of the two mixers 41 and 42 (that is, the amplitude demodulators 51 is coupled to the mixer 41, and the amplitude demodulators 52 is coupled to the mixer 42), to demodulate an amplitude of a down-converted signal to obtain an amplitude signal. The amplitude demodulators 51, 52 may be an envelope detector, which are composed of a Schottky diode, a resistor, and a capacitor and have simple circuit composition. The analysis device 53 is coupled to the two amplitude demodulators 51 and 52, to obtain, according to the amplitude signals output by the two amplitude demodulators 51 and 52, time points at which the pulse respectively passes through the two microwave resonators 31 and 32. Therefore, the analysis device 53 may calculate the difference between times for which the pulse passes through the two microwave resonators 31 and 32. Further, the analysis device 53 may further calculate a pulse wave velocity (PWV) according to the time difference. The health status of blood vessels may be estimated through the pulse wave velocity, and even a blood pressure value can be calculated. The analysis device 53 may be any computing device capable of performing the above calculation, such as a personal computer, a tablet computer, a smart phone, other embedded systems, or the like. The analysis device 53 includes an analog-to-digital conversion interface (such as a data acquisition (DAQ) card), to acquire the amplitude signal for subsequent digital signal processing.

In some embodiments, the signal processing unit 50 is directly implemented through the above analysis device 53. In other words, instead of using the above amplitude demodulators 51 and 52 of hardware for envelope detection, the envelope detection is implemented by software to obtain the amplitude signal and perform digital signal processing on the amplitude signal. The analysis device 53 still includes an analog-to-digital conversion interface (such as a data acquisition card, DAQ) configured to acquire a down-converted signal. The down-converted signal may be expressed as Equation 1, where A is an amplitude, $f_{IF}$ is a carrier frequency after down-converted by mixers 41 and 42, t is a time, and the amplitude signal is expressed as $x_1(t)$. The signal processing unit 50 squares the down-converted signal (Equation 2) and performs low-pass filtering to obtain the amplitude signal $x_1(t)$.

$$y(t)=[1+x_1(t)]A\ \sin(2\pi f_{IF}t) \quad \text{(Equation 1)}$$

$$(y(t))^2=\tfrac{1}{2}A^2+A^2x_1(t)+\tfrac{1}{2}A^2x_1^2(t)-\tfrac{1}{2}x_1^2(t)A^2\cos(4\pi f_{IF}t) \quad \text{(Equation 2)}$$

The embodiments of the present invention may further be implemented by using other digital envelope detection methods such as square law, coherent demodulation, Hilbert transform, and the like, and the present invention is not limited thereto.

In some embodiments, the pulse measurement device may further include other signal processing circuits, for example, a low-pass filter, a signal amplifier, and the like, which are coupled between the mixers 41 and 42 and the signal processing unit 50, to optimize signals entering the signal processing unit 50.

In some embodiments, the first signal source 10 and the second signal source 20 both include a signal generator and a power divider. The signal generator is configured to generate high-frequency signals, and the power divider is configured to divide the high-frequency signals into two signals for output, so that each of the microwave resonators 31 and 32 can receive the first high-frequency signals, and each of the mixers 41 and 42 can receive the second high-frequency signals. The power divider herein may be, for example, a Wilkinson power divider.

Next, the functions of the mixers 41 and 42 are to be described. The mixers 41 and 42 respectively mix the sensing signals of the microwave resonators 31 and 32 with the second high-frequency signals to output a down-converted signal. The down-converted signal is a low intermediate frequency signal, which facilitates signal acquisition and processing. Due to the nonlinear characteristics of the mixers 41 and 42, an intermodulation (IM) phenomenon is produced between the carrier (the first high-frequency signal) of the sensing signal and the second high-frequency signal. In other words, the down-converted signal may include an intermodulation signal. In Equation 3, inputs $V_{in}$ of the mixers 41 and 42 are expressed, where $A_1$ is an amplitude of the first high-frequency signal, $A_2$ is an amplitude of the second high-frequency signal, $\omega_1$ is the first high-frequency signal, $\omega_2$ is the second high-frequency signal, and t is a time. In Equation 4, outputs $V_{out}$ ($V_{in}$) of the mixers 41 and 42 are expressed. After Equation 3 is substituted into Equation 4, a second-order intermodulation term $k_2 A_1 A_2 \cos((\omega_1-\omega_2))$ and a fourth-order intermodulation term $\frac{3}{4} k_4 A_2^2 A_2^2 \cos((\omega_1-\omega_2))$ may be obtained respectively. The output of each order is converted to be expressed by power (dBm), and the amplitudes of the second-order intermodulation term (that is, a first-order intermediate frequency (IF)) and the fourth-order intermodulation term (that is, a second-order IF) are respectively expressed as that in Equation 5 and Equation 6. Since the main energy change is dominated by $A_1$, it can be seen that the second-order IF changes twice as much as the first-order IF, and the third-order IF changes three times, and so on. Since the amplitude of the intermodulation signal also increases with the order of a resonance frequency, this embodiment of the present invention uses the characteristic to amplify the signal.

$$V_{in} = A_1 \cos(\omega_1 t) + A_2 \cos(\omega_2 t) \quad \text{(Equation 3)}$$

$$V_{out}(V_{in}) = V_0 + k_1 V_{in} + k_2 (V_{in})^2 + k_3 (V_{in})^3 + \ldots \quad \text{(Equation 4)}$$

$$10 \log \frac{(k_2 A_1 A_2)^2}{Z_0 \times 10^{-3}} = \quad \text{(Equation 5)}$$
$$20 (\log k_2 + \log A_1 + \log A_2) - 10 \log(Z_0 \times 10^{-3})$$

$$10 \log \frac{(k_4 A_1^2 A_2^2)^2}{Z_0 \times 10^{-3}} = \quad \text{(Equation 6)}$$
$$20 (\log k_4 + 2 \log A_1 + 2 \log A_2) - 10 \log(Z_0 \times 10^{-3})$$

Figure 4:
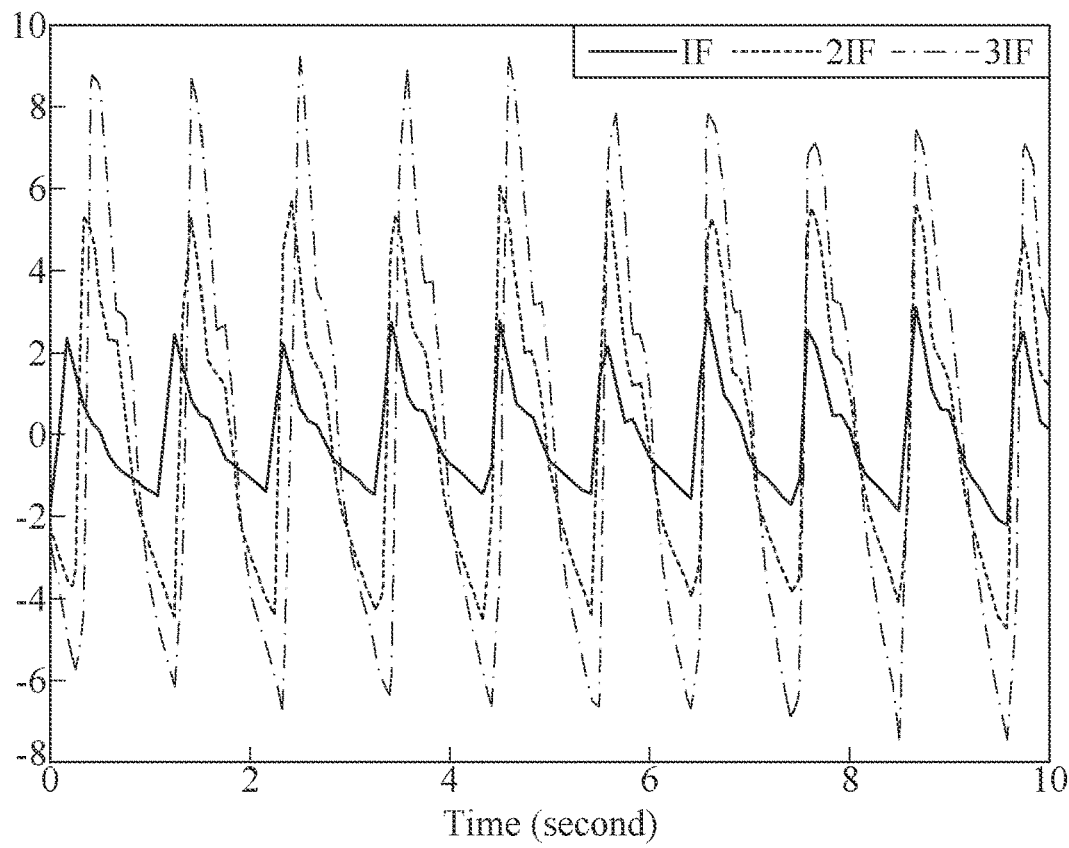
FIG. 4 is a schematic diagram of intermediate frequencies (IF) of each order according to an embodiment of the present invention.

FIG. 4 is a schematic diagram of intermediate frequencies (IF) of each order according to an embodiment of the present invention. It can be seen that a higher-order amplitude leads to a greater amplitude variation, so that the correct position can be measured more accurately, thereby improving the accuracy of measurement data and reducing errors. In some embodiments, the obtained high-order intermodulation signal may be differentiated (for example, second-order differential), so as to find out positions of peaks or valleys conveniently.

Next, the mixers 31 and 32 are to be described. In some embodiments, the microwave resonators 31, 32 may be implemented by a split-ring resonator (SRR) or a complementary split-ring resonator (CSRR).

Figure 5:
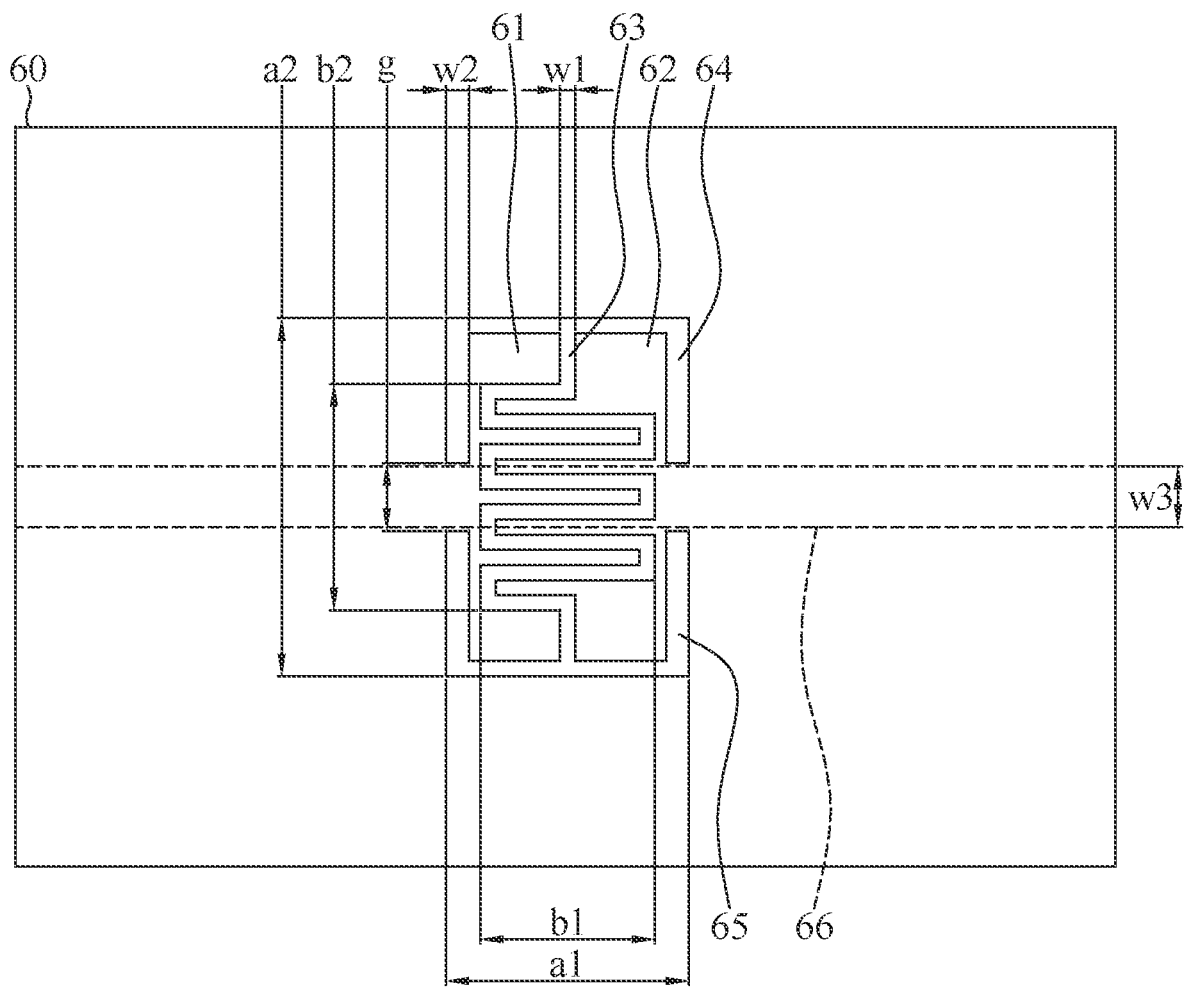
FIG. 5 is a top view of microwave resonators according to an embodiment of the present invention.

FIG. 5 is a top view of microwave resonators 31 and 32 according to an embodiment of the present invention. The microwave resonators 31 and 32 herein refer to interdigital capacitor shape resonators (ICSR). The interdigital capacitor shape resonator may be implemented by a printed circuit board, which includes a substrate 60. Two sides of the substrate 60 have conductive material parts and non-conductive material parts, respectively, so as to form required specific patterns. As shown in FIG. 5, a pattern on a front side of the substrate 60 is represented by a solid line, and a pattern on a reverse side of the substrate 60 is represented by a dashed line. The front side of the substrate 60 has two interdigital conductive portions 61 and 62 opposite to each other. The two interdigital conductive portions 61 and 62 are made of conductive materials. A gap 63 that continuously bends and extends is jointly defined between the two interdigital conductive portions 61 and 62. Slots 64 and 65 respectively extend from two ends of the gap 63. The gap 63 and the slots 64 and 65 are made of non-conductive materials. The slots 64, 65 surround the two sides of the interdigital conductive portion 61 and 62 to form a U-shape. The two U-shapes are opposite to each other, and positions closest to each other are separated by a distance but not connected. The continuously bent gap 63 can increase the inductance of the microwave resonators 31 and 32 to improve the sensitivity. The continuously bent area is also an area in which the electric field is concentrated (that is, a sensing area), so that the sensing area can also be expanded through a continuously bent structure, to facilitate alignment by the user. A microstrip line 66 is provided on the reverse side of the substrate 60, which is made of a conductive material and is used to transmit the first high-frequency signal. The microstrip line 66 crosses the gap 63. As an example, reference is made to Table 1 for dimensions of the interdigital capacitor shape resonator.

TABLE 1

| a1 | 5.6 millimeters | w1 | 0.3 millimeters |
|----|-----------------|----|-----------------|
| a2 | 8.2 millimeters | w2 | 0.5 millimeters |
| b1 | 4 millimeters   | w3 | 1.6 millimeters |
| b2 | 5.2 millimeters | g  | 1.5 millimeters |

Figure 6:
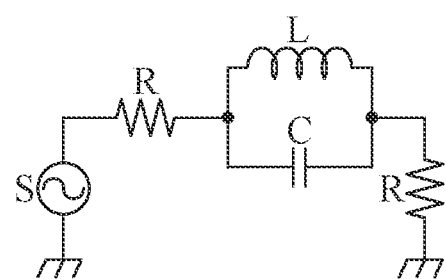
FIG. 6 is an equivalent circuit diagram of an interdigital capacitor shape resonator shown in FIG. 5.

FIG. 6 is an equivalent circuit diagram of an interdigital capacitor shape resonator shown in FIG. 5. The interdigital capacitor shape resonator may be equivalent to a Butterworth low-pass filter, and a resonant cavity may be equivalent to a circuit formed by an equivalent inductance L and equivalent capacitance C. Equivalent resistance R on two sides of the interdigital capacitor shape resonator is equivalent resistance of the microstrip line 66, and a signal S is a feeding signal (that is, the above first high-frequency signal). Referring to FIG. 5 and FIG. 6 together, parameters a1, a2, b1, and b2 may be used to adjust an inductance value of equivalent inductance L, and parameters w1, w2, and g may be used to adjust a capacitance value of equivalent capacitance C The parameter w3 is a width of the microstrip line 66.

Based on the above, according to the pulse measurement device provided by the embodiments of the present invention, the signal can be amplified through intermodulation, so that the accuracy of measured data can be improved, the error can be reduced, and the detection sensitivity can be improved through amplitude demodulation. Moreover, the two microwave resonators can be disposed at a local position, which is convenient for a user to place. In addition, the microwave resonator with the interdigital capacitor shape resonator can provide a better induced electric field, increase intensity of the sensing signal, and is more suitable for the user to use. Although the measurement of physiological parameters is used as an example for description above, the embodiments of the present invention are not limited to this application, and can also be applied to other fields.

What is claimed is:
1. A pulse measurement device, comprising:
a first signal source outputting a first signal;

two microwave resonators, wherein each of the microwave resonators is coupled to the first signal source, to form an electric field according to the first signal, and senses a variation in the electric field which is interfered by a pulse to obtain a sensing signal;

a second signal source outputting a second signal;

two mixers coupled to the second signal source, wherein each of the mixers is coupled to one of the two microwave resonators, to mix the sensing signal and the second signal to output a down-converted signal; and a signal processing unit coupled to the two mixers, to respectively demodulate amplitudes of the down-converted signals of the two mixers to obtain amplitude signals.

2. The pulse measurement device according to claim 1, wherein the signal processing unit comprises two amplitude demodulators and an analysis device, each of the amplitude demodulators is coupled to one of the two mixers, to demodulate the amplitude of the down-converted signal to obtain the amplitude signal, and the analysis device is coupled to the two amplitude demodulators, to obtain, according to the amplitude signals output by the two amplitude demodulators, time points at which the pulse respectively passes through the two microwave resonators.

3. The pulse measurement device according to claim 2, wherein at least one of the amplitude demodulators is an envelope detector.

4. The pulse measurement device according to claim 1, wherein the signal processing unit squares the down-converted signal and performs low-pass filtering to obtain the amplitude signal.

5. The pulse measurement device according to claim 1, the down-converted signal is a low intermediate frequency signal.

6. The pulse measurement device according to claim 1, wherein at least one of the microwave resonators is a split-ring resonator or a complementary split-ring resonator.

7. The pulse measurement device according to claim 1, wherein at least one of the microwave resonators is an interdigital capacitor shape resonator.

8. The pulse measurement device according to claim 7, wherein the interdigital capacitor shape resonator comprises two interdigital conductive portions opposite to each other, a gap that continuously bends and extends is jointly defined between the two interdigital conductive portions, and one slot extends from each of two ends of the gap.

9. The pulse measurement device according to claim 8, wherein the slots at the two ends of the gap surround two sides of the two interdigital conductive portions.

10. The pulse measurement device according to claim 8, wherein the slot is U- shaped.

\* \* \* \* \*

UNITED STATES PATENT AND TRADEMARK OFFICE
CERTIFICATE OF CORRECTION

| | | |
|---|---|---|
| PATENT NO. | : 11,579,175 B2 | Page 1 of 1 |
| APPLICATION NO. | : 17/212132 | |
| DATED | : February 14, 2023 | |
| INVENTOR(S) | : Chin-Lung Yang and Chia-Hui Chen | |

It is certified that error appears in the above-identified patent and that said Letters Patent is hereby corrected as shown below:

On the Title Page

Item (72) Inventors should read:
Chin-Lung YANG, Tainan (TW)
Chia-Hui CHEN, Tainan (TW)

Item (30) Foreign Application Priority Data should read:
Apr. 16, 2020 (TW).....................................109112875

Signed and Sealed this
Fourth Day of April, 2023

Katherine Kelly Vidal
*Director of the United States Patent and Trademark Office*